United States Patent [19]
Wright

[11] Patent Number: 5,542,564
[45] Date of Patent: Aug. 6, 1996

[54] POTPOURRI ASSEMBLY

[76] Inventor: Erlene Wright, 7291 American, Detroit, Mich. 48210

[21] Appl. No.: 264,070

[22] Filed: Jun. 22, 1994

[51] Int. Cl.⁶ ........................................................ A42B 1/24
[52] U.S. Cl. .......................................... 220/480; 2/209.13
[58] Field of Search .......................... 220/480; 2/209.14, 2/209.13

[56] References Cited

U.S. PATENT DOCUMENTS

| | | |
|---|---|---|
| D. 72,494 | 4/1927 | Peters . |
| D. 120,586 | 5/1940 | Hall . |
| D. 179,106 | 10/1956 | Wittcoff . |
| D. 188,033 | 5/1960 | Simon . |
| D. 270,300 | 8/1983 | Jarvis . |
| 1,139,418 | 5/1915 | Hiller . |
| 1,545,300 | 7/1925 | Alea . |
| 2,358,708 | 9/1944 | Halmos . |
| 3,031,681 | 5/1962 | Hoeflich . |
| 4,268,918 | 5/1981 | Lee . |
| 5,253,368 | 10/1993 | Blake .................. 2/209.13 X |
| 5,287,559 | 2/1994 | Christiansen et al. ............. 2/209.13 X |
| 5,410,761 | 5/1995 | Connelly et al. ................. 2/209.13 X |
| 5,452,479 | 9/1995 | Mostert ............................. 2/209.13 X |
| 5,465,426 | 11/1995 | Beaton ............................... 2/209.13 X |

FOREIGN PATENT DOCUMENTS 232492  4/1925  United Kingdom .

Primary Examiner—Steven M. Pollard
Attorney, Agent, or Firm—Richard C. Litman

[57] ABSTRACT

A potpourri assembly includes a decorative display hat. The hat is generally of the straw type, with a dome-like crown and a substantial brim. The assembly is preferably displayed with its brim vertical and its crown facing forward. The assembly may be secured in this position by means of a loop, of ribbon or similar material, that lies flush to the rear of the brim at the top of the hat. Potpourri sits within the crown of the hat, and is secured by a circular fabric covering. The fabric covering is attached to the outer edge of the crown opening. Preferably, the circular fabric covering includes two approximately semicircular, approximately equal pieces of fabric, one upper piece and one lower piece. The straight edge of the lower piece overlaps the straight edge of the upper piece to form an insertion opening for the potpourri. A circumferential piece of fabric lies atop the curved edge of the circular fabric covering in order to provide a finished look.

13 Claims, 6 Drawing Sheets

5,542,564

POTPOURRI ASSEMBLY

BACKGROUND OF THE INVENTION

1. Field of the Invention

The present invention relates to a decorative display hat that securely and attractively holds potpourri.

2. Description of the Prior Art

Many hats on the market are attractive and/or visually intriguing. Most of these hats are, of course, intended to be worn on the head, but there are a number which are designed to be displayed in the home. These may be purchased at such places as craft fairs, boutiques, and bazaars. Another well known craft item available in such venues is potpourri, a pleasant smelling mixture composed generally of spices and dried flowers, bark, and citrus peels. There are also available a variety of holders for potpourri, some designed to be hung and others to rest upon surfaces. None of the prior art, however, discloses a decorative display hat, capable of being hung or of resting on a surface, that is augmented in an attractive fashion to hold potpourri.

Numerous patents have issued for visually intriguing headwear. For instance, U.S. Pat. No. 3,031,681, issued to Victor T. Hoeflich on May 1, 1962, discloses a disposable tiara-like item designed to be worn on the head at festive gatherings. U.S. Pat. No. Des. 270,00, issued to Robert L. Jarvis on Aug. 30, 1983, shows an ornamental hat band that ties around the bottom part of the crown of a hat.

Some visually intriguing headwear comes in the form of caps. For example, U.S. Pat. No. Des. 72,494, issued to Mina L. Peters on Apr. 19, 1927, displays an open, lacy boudoir cap. A swimming cap with intricate fringed attachments is shown in U.S. Pat. No. 1,139,418, issued to Elsie Hiller on May 11, 1915. U.S. Pat. No 4,268,918, issued to Lois E. Lee on May 26, 1981, discloses a baseball-type cap, with moving parts, that mimics the appearance of one of a variety of animals.

There are also many attractive hats made of straw or suchlike. U.S. Pat. No. 1,545,3, issued to José Alvarez Alea on Jul. 7, 1925, discloses a straw or rattan hat whose brim has a curled flange. Decorated hats that appear to be made of straw are shown in U.S. Pat. No. Des. 179,106, issued to Edward Wittcoff on Oct. 30, 1956, and U.S. Pat. No. Des 188,333, issued to Ethel Simon on May 24, 1960.

Some patents are concerned with versatile hats. U.S. Pat. No. 2,358,708, issued to Klara Halmos on Sep. 19, 1944, discloses a hat whose brim incorporates elastic cord that allows the hat to be configured in a variety of ways. British Patent Specification No. 232,492, accepted on Apr. 23, 1925 in the name of Doris Sophie Munn, discusses a reversible hat with a detachably secured brim. In a related vein, a convertible purse is shown in U.S. Pat. No. Des. 120,586, issued to Mercedes Hall on May 14, 1940.

None of the above inventions and patents, taken either singly or in combination, is seen to describe the instant invention as claimed.

SUMMARY OF THE INVENTION

The present invention concerns an improved decorative display hat. The hat is augmented to hold potpourri. The hat is of the type having a crown and a brim, with the crown being substantially dome-like and the brim being of substantial size, large enough to provide a framing effect. Orienting the hat with the brim vertical, the front of the hat may be decorated with various attractive objects. The crown ends in a circular opening at the rear of the hat. Over the circular opening is a circular fabric 10 covering, attached to the hat by glue or thread. In the primary embodiment, the fabric covering includes two approximately semicircular pieces of fabric, of approximately equal size. The straight edge of the lower piece overlaps the straight edge of the upper piece to form an insertion opening. Secured on top of the curved edge of the circular fabric covering is a circumferential piece of fabric, which hides the curved edge below. A loop is located above approximately the midpoint of the upper curved edge of the circular fabric covering. The loop serves as hanging means if the assembly is displayed upright. Potpourri is inserted into the crown of the hat through the insertion opening.

Accordingly, it is a principal object of the invention to provide an attractive potpourri assembly.

It is another object of the invention to provide an improved decorative display hat, with attractive objects visible from all sides of the hat.

It is an object of the invention to provide a potpourri assembly capable of being suspended and of resting on a flat surface.

It is a further object of the invention to provide a potpourri assembly with a fabric covering that secures potpourri within the assembly.

It is another object of the invention to provide a potpourri assembly with an insertion opening that allows for easy insertion and withdrawal of potpourri.

Still another object of the invention is to provide a potpourri assembly with an insertion opening whose edges may be secured together.

Yet another object of the invention is to provide a potpourri assembly which allows a pleasing amount of scent to spread to its surroundings.

It is an object of the invention to provide improved elements and arrangements thereof in an apparatus for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
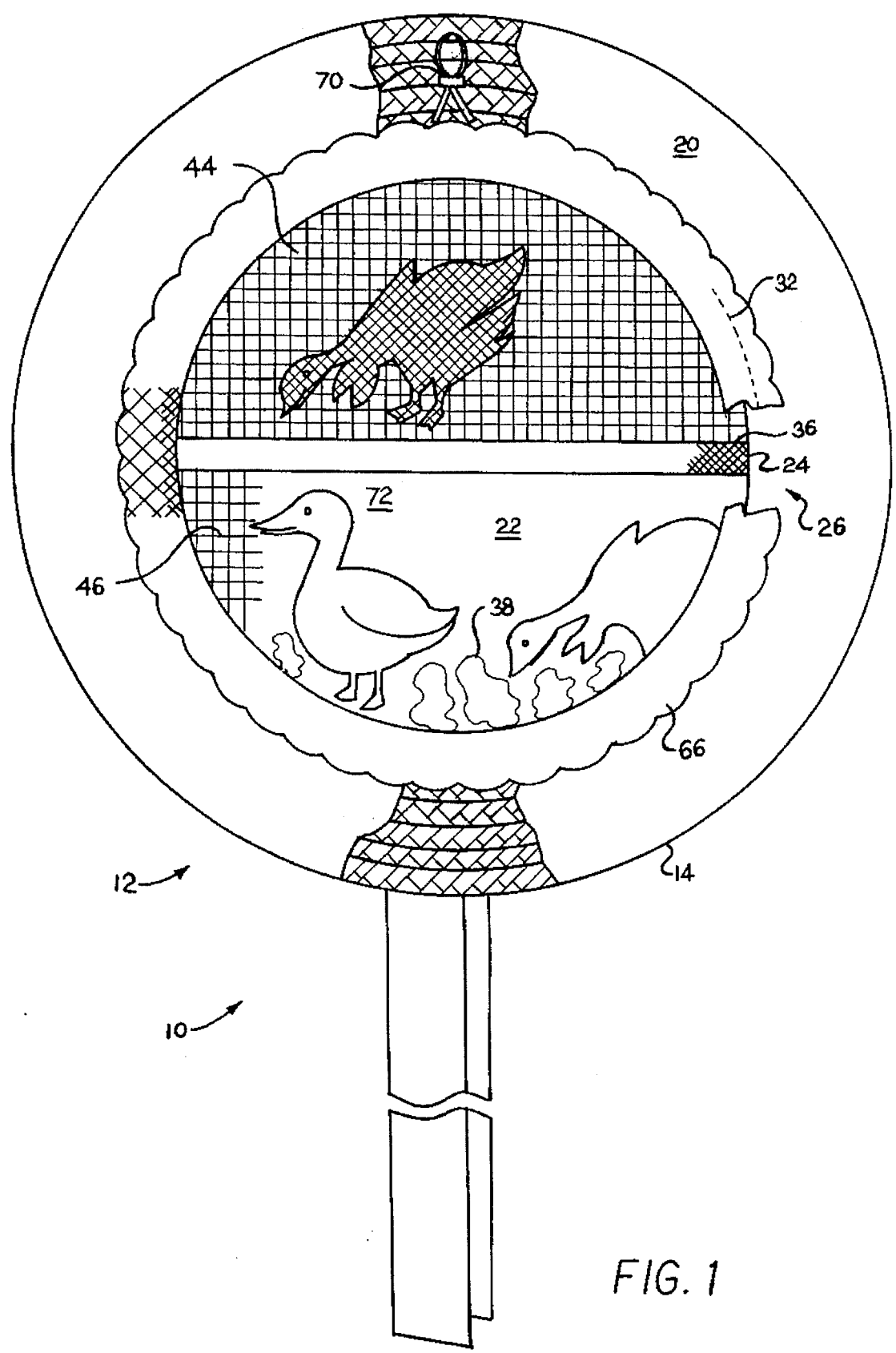
FIG. 1 is a rear view of a potpourri assembly according to the present invention.
Figure 4:
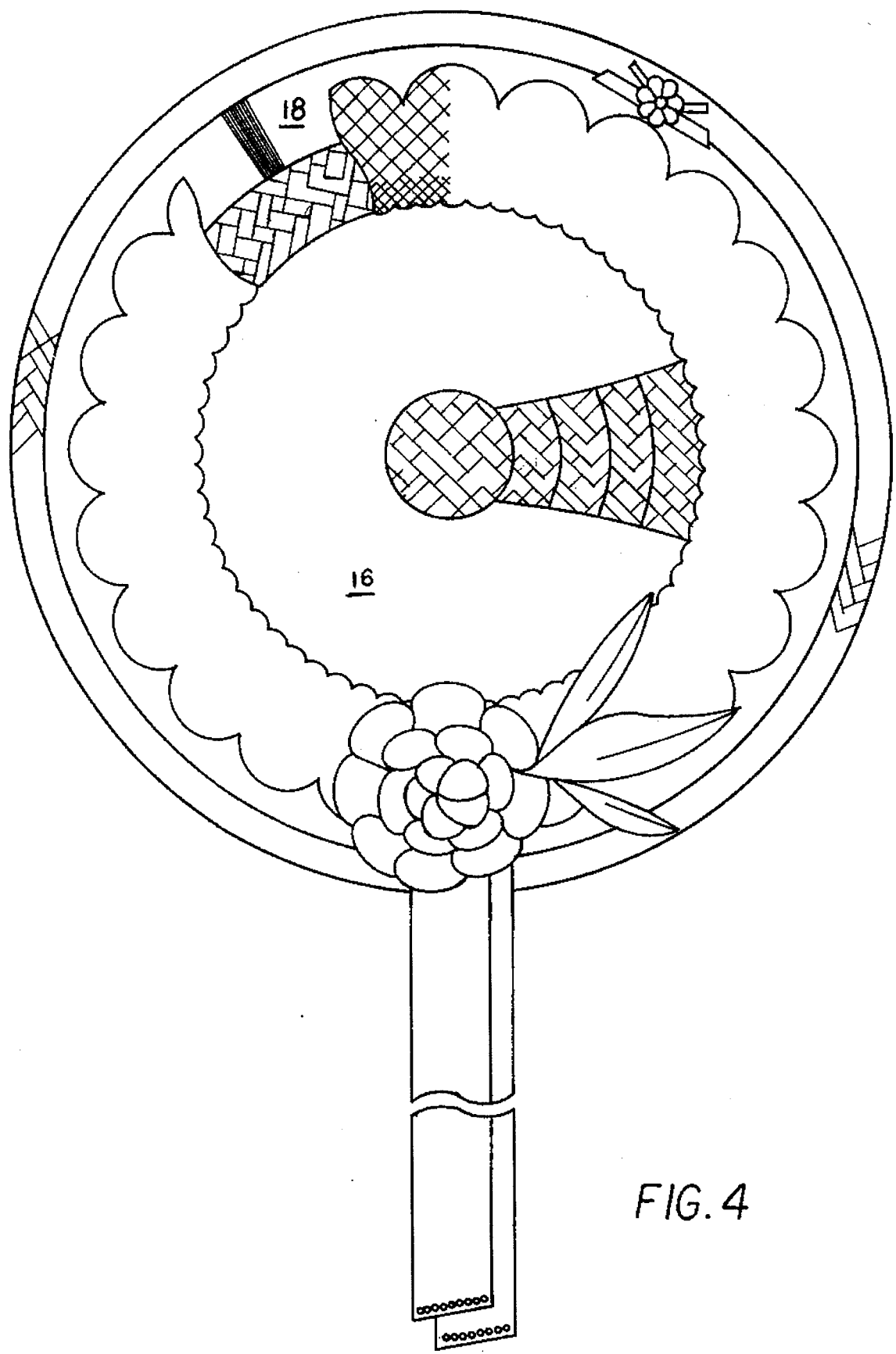
FIG. 4 is a front view of the present invention.

Referring now to FIG. 1, the present invention is a potpourri assembly, generally designated 10, which is particularly adapted to holding potpourri while at the same time presenting an unusual and attractive appearance. The mainstay of the assembly is a hat 12. The hat 12, which is preferably made of straw, has a brim 14 and a crown 16, the latter shown in FIG. 4. The brim 14 is of a substantial size, extending far enough to give a framing effect with respect to the crown 16. The brim 14 has a front 18 and a rear 20. The front 18, shown in FIG. 4, may be plain or may be arrayed with decorative object, such as dried or fabric flowers, lace or ribbon, or artificial fruit. The crown 16 is of a typical dome-like shape, and has a circular opening 22 at the rear 20 of the brim 14.

Figure 3:
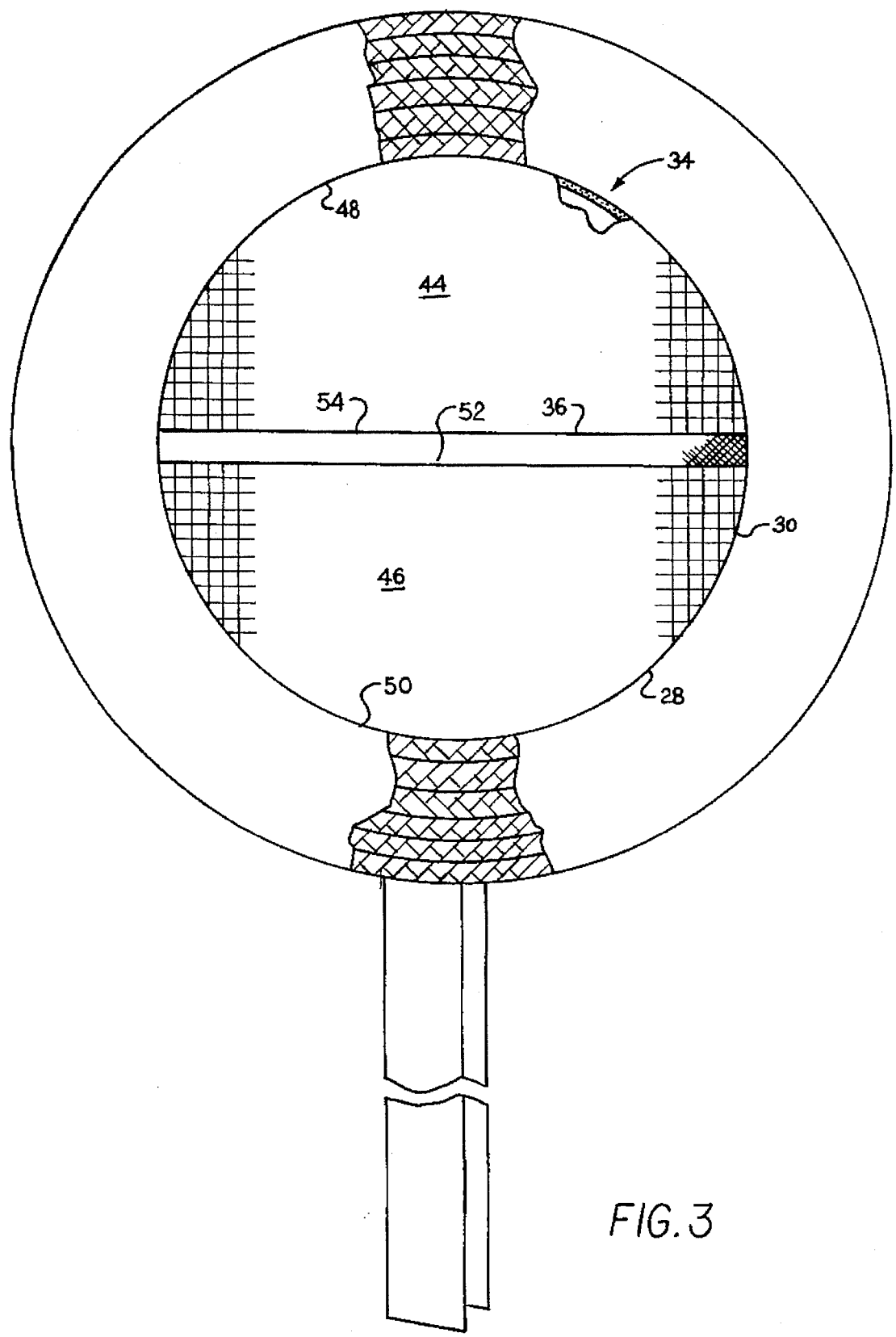
FIG. 3 is a rear view, partly in section, similar to FIG. 1.

On the perimeter 24 of the circular opening 22 of the crown 16 there is attached a circular fabric covering 26, which extends over the whole of the circular opening 22. As shown in FIG. 3, the outer edge 28 of the circular fabric covering 26 is secured to the perimeter 24 by attachment means 30, which may be, for instance, thread stitching 32, partially shown in FIG. 1, or glue 34. In the case of thread 32, either a color that blends in with the fabric or hat material or a color that contrasts may be chosen. Thread is herein used to include both thinner and thicker lengths of fibrous material.

The fabric covering 26 has an insertion opening 36 for the potpourri 38. The insertion opening 36 may be a slit 39, as in FIG. 8, cut in the fabric covering; may be a slot 40, as in FIG. 7, formed by overlapping edges 52, 54 within the fabric covering 26; or may be a slot 41, as shown in FIG. 6, shaped by proximate but non-overlapping edges 42, 43 within the fabric covering 26.

As shown most clearly in FIGS. 1 and 3, the fabric covering 26 may come in two pieces 44, 46, these being an upper piece of fabric 44 and a lower piece of fabric 46, both approximately semicircular and approximately equal in size. Each of these pieces has a curving edge, 48, 50, respectively, and a straight edge, 52, 54, respectively. One or both of the two pieces of fabric 44, 46 may be slightly greater than semicircular, in order to make their straight edges 52, 54 overlap, thus to form an insertion opening 36.

Figure 7:
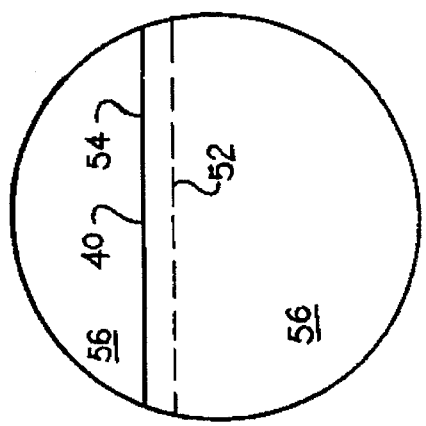
FIG. 7 is a detail view of another alternative embodiment of the circular fabric covering of the present invention.
Figure 6:
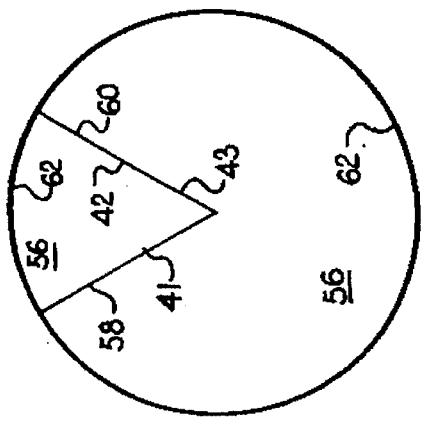
FIG. 6 is a detail view of an alternative embodiment of the circular fabric covering of the present invention.
Figure 8:
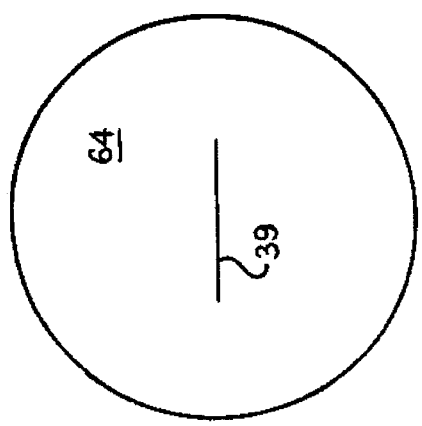
FIG. 8 is a detail view of another alternative embodiment of the circular fabric covering of the present invention.

Alternatively, one or both of the pieces of fabric 44, 46 may be a truncated circle 56, substantially greater than semicircular, as shown in FIG. 7, or having two straight edges 58, 60 and one curving edge 62, as shown in FIG. 6. In another embodiment, shown in FIG. 8, the fabric covering 26 may be of only one piece 64, with an insertion opening 39 cut in it.

Returning to FIG. 1, secured atop the outer edges 28 of the circular fabric covering 26 is a circumferential piece of fabric 66, which gives the rear of the potpourri assembly 10 a finished look. Alternatively, the circumferential piece of fabric 66 may be integral to the circular fabric covering 26.

Figure 2:
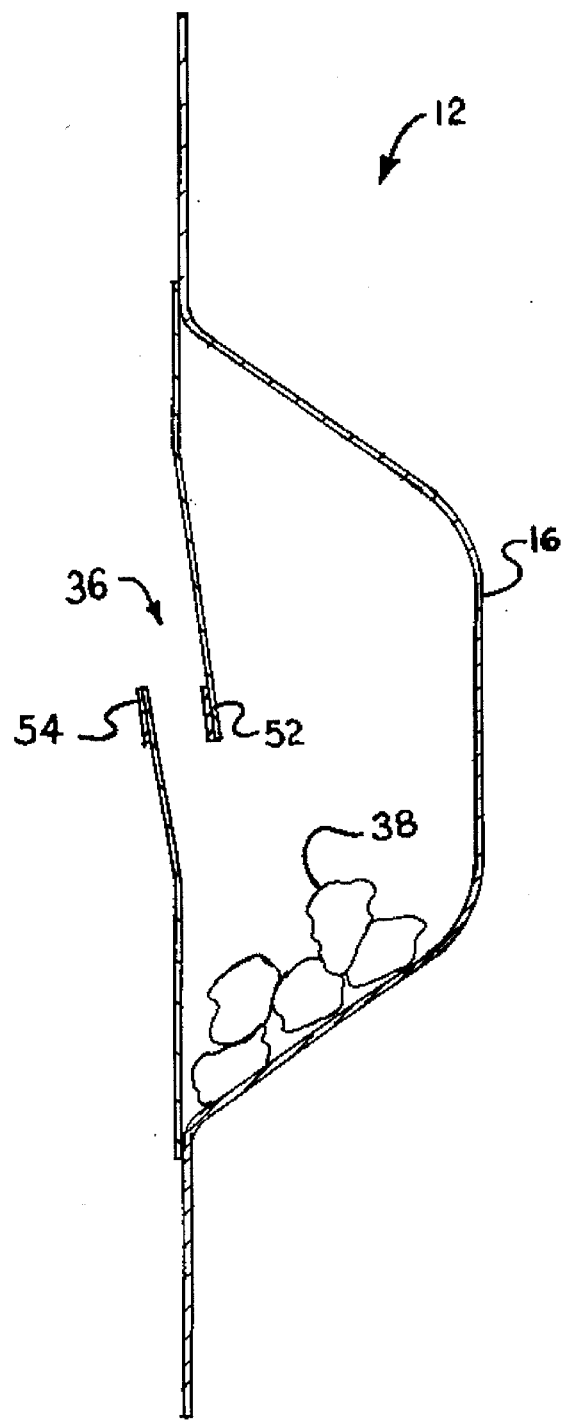
FIG. 2 is a cross-sectional detail of the crown area of the present invention.

As shown in FIG. 2, potpourri 38, of variable kind and number of pieces, is located in the crown 16 of the hat 12. The insertion opening 36 provides the means for inserting it. The circular fabric covering 36 prevents the potpourri 38 from escaping when the potpourri assembly 10 is on display.

Figure 9:
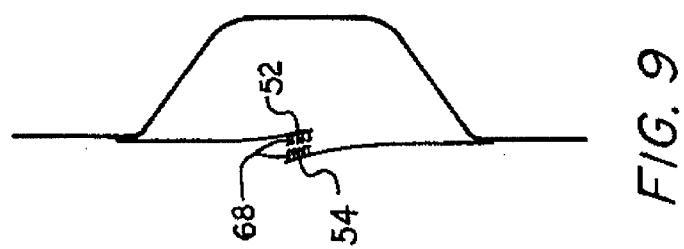
FIG. 9 is a cross-sectional detail view of the crown area of an alternative embodiment of the present invention.

In an alternative embodiment, shown in FIG. 9, the edges 52, 54 of the insertion opening 36 may be secured together after the potpourri 38 is placed inside. This is accomplished through securing means 68 on the edges. The securing means 68 may include, for example, hook and loop material.

Display is generally accomplished by attaching a loop 70 to a nail or other suspension means (not shown). The loop 70 is located on the rear 20 of the brim 14 of the hat 12, near the midpoint of the curving edge 48 of the upper approximately semicircular piece 44, and lies substantially flat to the brim 14. When slid over a horizontally projecting nail, the loop 70 supports the potpourri assembly 10 with the brim 14 mainly vertical.

It is envisioned that most commonly the rear 20 of the brim 14 will be facing a wall and the crown 16 will project outward into the room of display. If it is so desired, the potpourri assembly 10 may be suspended in midair from a suitable support, such that both the front and rear of the assembly are displayed. Another possibility is for the assembly to rest on a flat surface on either its crown 16 or rear 20 of brim 14.

There are a number of kinds of fabric that may be used in the potpourri assembly 10. The primary embodiment uses lace 72 for the circular fabric covering 26 and circumferential piece of fabric 66 and ribbon for the loop 70. FIG. 1, for example, shows lace displaying bird figures for the circular fabric covering 26, plain lace for the circumferential piece of fabric 66, and ribbon for the loop 70. Alternative embodiments may use fabric that is sheer, such as nylon, or opaque.

Figure 5:
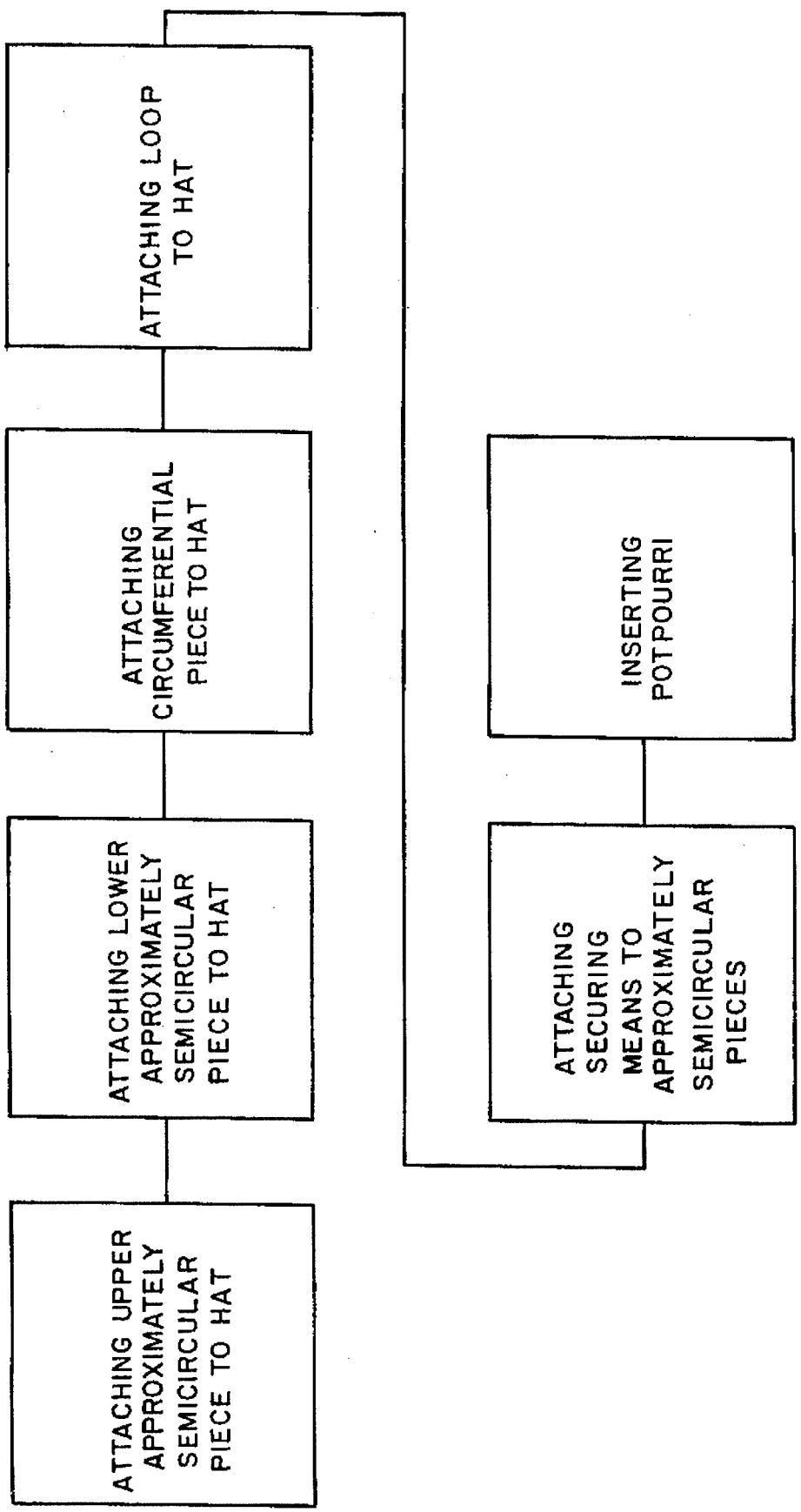
FIG. 5 is a block diagram of an assembly process of the present invention.

Steps involved in constructing a potpourri assembly 10 are diagrammed in FIG. 5. Construction begins with attaching the circular fabric covering 26 to the hat 12. In the primary embodiment, the fabric covering is originally two pieces, the upper approximately semicircular piece 44 and the lower approximately semicircular piece 46. The upper piece 44 is secured to the hat 12 first, with its curving edge 48 being either glued or sewn to the top arc of the outer perimeter 24 of the crown circular opening 22. The lower piece 46 is next either glued or sewn to the bottom arc of the outer perimeter 24 of the crown circular opening 22. The two pieces 44, 46 together are of such a size that the straight edge 54 of the lower piece 46 overlaps slightly the straight edge 52 of the upper piece 44, thus forming the insertion opening 38.

The circumferential fabric 66 is attached atop the outer edge 28 of the circular fabric covering 26 such that the edge 28 is hidden from view. This attaching is also done by sewing or gluing. In alternative embodiments, the upper and lower pieces 44, 46 may be integral with one another, or the circumferential piece 66 may be integral with both of them. Also, either or both of the upper and lower approximately semicircular pieces 44, 46 may be a truncated circle 56.

The loop 70 is attached to the rear side 20 of the brim 14, near the midpoint of the curving edge 48 of the upper piece 44. Glue 34 or thread 32 is again used.

In an alternative embodiment, securing means 68 are attached to the approximately semicircular pieces 44,46 at the edges of the insertion opening 38. Hook and loop material may be used.

After all construction steps are completed, potpourri may be inserted into the crown through the insertion opening.

Obviously, some of these steps may be performed in alternative orders.

It is to be understood that the present invention is not limited to the embodiments described above, but encompasses any and all embodiments within the scope of the following claims.

I claim:
1. A potpourri assembly comprising:
   a hat having a substantial brim and a crown, said brim having a front and a rear, and said crown being substantially dome-like and having a substantially circular opening at said rear of said brim, said circular opening having a perimeter,
   attachment means, a circular fabric covering having an outer edge, said circular fabric covering secured to said perimeter of said circular opening by said attachment means, said circular fabric covering, covering said circular opening, means defining an insertion opening, said insertion opening located within said circular fabric covering, a circumferential piece of fabric, said circumferential piece of fabric secured atop said outer edge of said circular fabric covering, and a loop, said loop secured to said rear of said brim.

2. The potpourri assembly according to claim 1, wherein said circular fabric covering comprises two substantially semicircular pieces of fabric, these being an upper piece and a lower piece, said pieces of fabric being approximately equal in size and each of said pieces of fabric having a curved edge and a straight edge, with said straight edge of said lower piece of fabric overlapping slightly said straight edge of said upper piece of fabric to form said insertion opening.

3. The potpourri assembly according to claim 2, further including potpourri pieces, said potpourri pieces located within said substantially dome-like crown and said potpourri pieces being restrained by said circular fabric covering.

4. The potpourri assembly according to claim 2, selected ones of said pieces of fabric being lace.

5. The potpourri assembly according to claim 2, selected ones of said pieces of fabric being sheer.

6. The potpourri assembly according to claim 2, selected ones of said pieces of fabric being opaque.

7. The potpourri assembly according to claim 2, further including securing means, said securing means attached to said approximately semicircular pieces.

8. The potpourri assembly according to claim 2, said securing means further including hook and loop material.

9. The potpourri assembly according to claim 2, said attachment means being glue.

10. The potpourri assembly according to claim 2, said attachment means being thread.

11. The potpourri assembly according to claim 1, wherein said circumferential piece of fabric is integral with said circular fabric covering means.

12. The potpourri assembly according to claim 1, wherein said circular fabric covering means includes two pieces of fabric, said pieces of fabric being truncated circles.

13. A potpourri assembly comprising:

a hat having a substantial brim and a crown, said brim having a front and a rear, and said crown being substantially dome-like and having a circular opening at said rear of said brim, said circular opening having a perimeter, attachment means, a circular fabric covering having an insertion opening, said circular fabric covering including two approximately semicircular pieces of fabric, these being upper piece and a lower piece, said fabric being lace, said semicircular pieces of fabric being approximately equal in size and each said approximately semicircular piece of fabric having a curved edge and a straight edge, with said straight edge of said lower approximately semicircular piece of fabric overlapping slightly said straight edge of said upper approximately semicircular piece of fabric to form said insertion opening, said curved edges of said approximately semicircular pieces of fabric secured to said perimeter of said circular opening by said attachment means, said circular fabric covering, covering said circular opening, a circumferential piece of fabric, said fabric being lace, said circumferential piece of fabric secured atop said curved edges of said approximately semicircular pieces of fabric, a loop, said loop secured to said rear of said brim, and potpourri pieces, said potpourri pieces located within said substantially dome-like crown and said potpourri pieces being restrained by said circular fabric covering.

* * * * *